United States Patent
Hossainy et al.

(10) Patent No.: US 8,241,653 B1
(45) Date of Patent: *Aug. 14, 2012

(54) PIEZOELECTRICITY MODULATED RELEASE RATE OF DRUG FROM A COATING

(75) Inventors: Syed Faiyaz Ahmed Hossainy, Fremont, CA (US); Gordon Stewart, San Francisco, CA (US); William E. Webler, San Jose, CA (US); Benjamyn Serna, Gilroy, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/890,905

(22) Filed: Aug. 7, 2007

(51) Int. Cl.
*A61F 2/02* (2006.01)
(52) U.S. Cl. .................................................. 424/423
(58) Field of Classification Search .................. None
See application file for complete search history.

(56) References Cited

U.S. PATENT DOCUMENTS

| | | | |
|---|---|---|---|
| 4,427,609 A | 1/1984 | Broussoux et al. | |
| 4,733,665 A | 3/1988 | Palmaz | |
| 4,800,882 A | 1/1989 | Gianturco | |
| 4,886,062 A | 12/1989 | Wiktor | |
| 5,505,870 A * | 4/1996 | Yoo et al. | 252/62.9 PZ |
| 5,796,207 A | 8/1998 | Safari et al. | |
| 7,799,268 B2 * | 9/2010 | Tofail et al. | 264/675 |
| 2005/0158360 A1 | 7/2005 | Falotico et al. | |
| 2006/0129216 A1 | 6/2006 | Hastings et al. | |

OTHER PUBLICATIONS

U.S. Appl. No. 11/890,904, Hossainy et al., filed Aug. 7, 2007.
"Thermally Stable Piezoelectric and Pyroelectric Polymers", NASA Tech Brief, 2 pgs. May 2006.
Bouaziz et al., Biomaterials, 18(2) pp. 107-112 (1997).
Kipshidze et al., "Role of the Endothelium in Modulating Neointimal Formation", J. of Am. Col. of Cartdiology vol. 44, No. 4 pp. 733-739 (2004).
Martin et al., "Enhancing the biological activity of immobilized osteopontin using a type-1 collagen affinity coating", Binding of OPN to type 1 collagen, pp. 10-19 (2004).
Serruys et al., "A Randomized Comparison of the Value of Additional Stenting After Optimal Balloon Angioplasty for Long Coronary Lesions", J. of Am. Col. of Cartdiology vol. 39, No. 3 pp. 393-399 (2002).
Spagnuolo et al., "Gas1 is induced by VE-cadherin and vascular endothelial growth factor and inhibits endothelial cell apoptosis", Blood vol. 103, No. 8, pp. 3005-3012 (2004).
Švorčík et al., "Effect of Electrical Field on Dipoles in Polymer Composites" J. of Applied Polymer Science, vol. 91, pp. 40-45 (2004).
Völkel et al., "Targeting of immunoliposomes to endothelial cells using a single-chain Fv fragments directed against human endoglin (CD105)", Biochimica et Biophysica Acta 1663 pp. 158-166 (2004).
Yue et al., "1000 V/μm pulsed poling technique for photolime-gel electro-optic polymer with room-temperature repoling feature", Applied Physics Letters vol. 72, No. 26, pp. 3420-3421 (1998).

* cited by examiner

*Primary Examiner* — Carlos Azpuru
(74) *Attorney, Agent, or Firm* — Squire Sanders (US) LLP

(57) ABSTRACT

Provided herein is a method of controlling release rate of a bioactive agent from an implantable medical device comprising a coating, a coating on the implantable device and a method of making the coating.

20 Claims, 1 Drawing Sheet

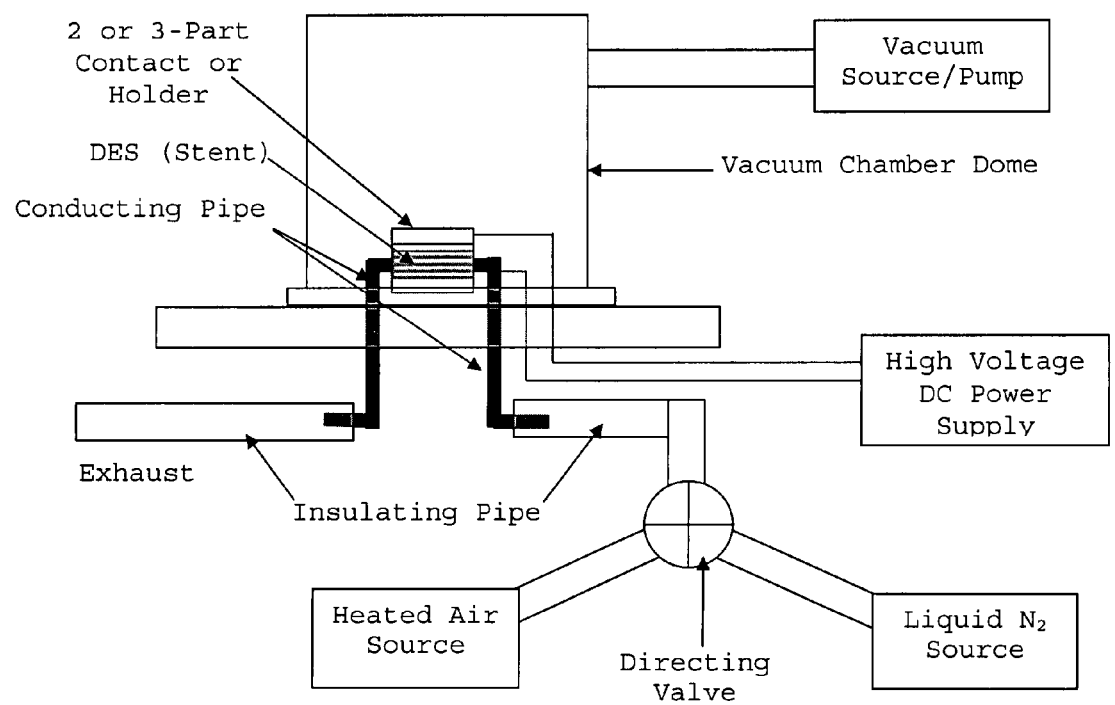

PIEZOELECTRICITY MODULATED RELEASE RATE OF DRUG FROM A COATING

BACKGROUND OF THE INVENTION

1. Field of the Invention

The invention is generally related to coatings for implantable medical devices, such as drug delivery vascular stents for controlling the release rate of bioactive agents from the polymer matrix. This invention more particularly relates to piezoelectricity modulation of release rate of bioactive agents from the polymer coatings.

2. Description of the Related Art

Biomaterials research is continuously striving to improve the compositions from which medical articles, such as medical devices and coatings for medical devices, are produced. An example of a medical article is an implantable medical device.

A stent is an example of an implantable medical device that can benefit from improvements, such as a coating that can be used as a vehicle for delivering pharmaceutically active agents in a predictable manner. Stents can act as a mechanical intervention to physically hold open and, if desired, expand a passageway within a subject. Typically, a stent may be compressed, inserted into a small vessel through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within vascular lumens, such as the lumen of a coronary artery.

Stents are also being developed to provide a local delivery of agents. Local delivery of agents is often preferred over systemic delivery of agents, particularly where high systemic doses are necessary to achieve an effect at a particular site within a subject—high systemic doses of agents can often create adverse effects within the subject. One proposed method of local delivery includes coating the surface of a medical article with a polymeric carrier and attaching, an agent to, or blending it with, the polymeric carrier.

Agent-coated stents have demonstrated dramatic reductions in the rates of stent restenosis by inhibiting tissue growth associated with the restenosis. The process of restenosis in coronary artery disease is derived from an interplay of several implant-centered biological parameters. These are thought to be the combination of elastic recoil, vascular remodeling, and neointimal hyperplasia. Since restenosis is a multifactorial phenomenon, the local delivery of agents from a stent can be improved through the design of a release rate profile that would deliver agents as needed from the stent in a controlled manner.

Therefore, there is a need for a coating that provides controlled release of a bioactive agent and improved mechanical properties.

The embodiments of the present invention address these concerns as well as others that are apparent to one having ordinary skill in the art.

BRIEF SUMMARY OF THE INVENTION

In one embodiment, the present invention describes a method of controlling release rate of a bioactive agent from an implantable medical device, the method comprising:

a) providing a coating on an implantable medical device, the coating comprising the bioactive agent and one or more piezoelectric polymer(s) or material(s) comprising crystal lamella;

b) exposing the coating to a low temperature to increase crystallinity of the coating; and c) subjecting the coating to a high DC voltage to polarize the piezoelectric polymer(s) or material(s) so as to increase the population of the crystal lamella by converting the amorphous lamella into crystal lamella, thereby reducing the release rate of the bioactive agent from the coating.

In other embodiments, the coating is heated at a temperature which is below body temperature or the coating is exposed at 0° C. or the coating is heated at room temperature.

In one embodiment, the above coating comprises a piezoelectric polymer. The piezoelectric polymer is a copolymer comprising units derived from fluoro vinyl monomers. The piezoelectric polymer comprises poly(vinylidene fluoride) (PVDF) or poly(vinylidene fluoride-co-hexafluoropropylene) (PVDF-HFP).

In some embodiments, the piezoelectric polymer is selected from poly(vinylidene fluoride) (PVDF), copolymers of PVDF such as poly(vinylidene fluoride-co-hexafluoropropylene) (PVDF-HFP), poly(vinylidene fluoride-co-trifluoroethylene) (PVDF-TrFE), poly(vinylidene fluoride-co-tetrafluoroethylene) (PVDF-TFE), polyamides, nylon-11, polyureas, polyurea-9, liquid crystalline polymers, biopolymers such as collagen, polypeptides, poly-methylglutamate, poly-benzyl-L-glutamate, synthetic polypeptides, oriented films of DNA, poly-lactic acid, chitin, poly(vinyl chloride) (PVC), poly(vinyl acetate) (PVAc), poly(acrylonitrile) (PAN), poly(vinylidenecyanide-co-vinyl acetate) (PVDCN-VAc), poly(vinylidenecyanide-co-vinyl benzoate) (PVDCN-VBz), poly(vinylidenecyanide-co-methyl methacrylate) (PVDCN-MMA), poly(phenylethernitrile) (PPEN), poly(1-bicyclobutanecarbonitrile), nitrile-substituted polyimides such as (—CN) APB/ODPA polyimide, aromatic polyamides, aliphatic polyurethane, polyparaxylene, poly-bis-chloromethyloxetane (Pentone), polysulfone, polyvinyl fluoride, cyanoethyl cellulose, or combinations thereof.

In another embodiment, the above coating comprises a polarized piezoelectric material. The piezoelectric material comprises a piezoelectric ceramic or a piezoelectric polymer-ceramic composite.

In certain embodiments, the implantable medical device is stent.

In some embodiments, the coating described herein further comprises at least one bioactive agent. The bioactive agent is selected from paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, prodrugs thereof, co-drugs thereof, and combinations thereof.

In certain embodiment, the present invention describes a coating on an implantable medical device, comprising:

at least one bioactive agent and at least one polarized piezoelectric polymer or material, wherein the polarized piezoelectric polymer or material comprises an increased population of crystal lamella resulting in a reduction of release rate of the bioactive agent from the coating.

In some embodiments, the coating is subjected to the DC high voltage which can be from about 50 to about 80 million volts per meter of coating thickness.

In other embodiments, the present invention describes a method, comprising implanting in a patient an implantable medical device comprising the coating, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

In another embodiments, the present invention describes a method, comprising implanting in a patient an implantable medical device comprising the coating, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

BRIEF DESCRIPTION OF THE DRAWINGS

FIG. 1 illustrates presently preferred direct contact piezoelectric polarization method using PVDF-HFP polymer.

DETAILED DESCRIPTION OF THE INVENTION

As discussed in more detail below, the embodiments of the present invention generally encompass controlling the morphology of a polymer matrix using piezoelectric polarization to improve the performance characteristics of an implantable medical device. More particularly, the present invention provides a coating on an implantable medical device which controls release of a bioactive agent from the coating.

Modulation of Drug Release

Provided herein is a method of modulating rate of release of an agent from a coating by piezoelectricity and the method of making and using the coating. The piezoelectric coating includes a piezoelectric polymer or material.

Piezoelectric polymer, such as poly(vinylidene fluoride-co-hexafluoropropylene) (PVDF-HFP), can have a microstructure that contains random stacks of amorphous and crystal lamella. Due to the tight/highly ordered structure of the crystal lamella relative to the amorphous lamella, diffusion of a drug will preferentially occur through the amorphous lamella. Increasing the portion of the microstructure that contains the crystal lamella can reduce the drug release rate. Exposing the stent to a very low temperature (e.g., liquid nitrogen or dry ice) can cause the coating polymer to assume a very low energy state, which favors the formation of crystal lamella. Further, exposing the stent to a very low temperature (e.g., liquid nitrogen or dry ice) also causes the PVDF-HFP polymer to contract, inducing strains into the polymer microstructure that tends to align the crystal lamella.

The crystal lamella microstructure of PVDF-HFP and other fluorinated polymers form a class of polymers called ferroelectric polymers that can exhibit piezoelectric and pyroelectric activity, which is especially strong in an aligned crystal lamella. This activity is induced by the application of a strong electric field across the polymer, which causes a rotation of the polymer's molecular structure such that its fluorine atoms are all on one side of the molecule (transition from a non-polar alpha phase to a polar beta phase). This polarization is not retained by the amorphous lamella after the electric field is removed; however, it is retained by the crystal lamella. Polarizing of a crystal lamella will stabilize its crystal structure, such that new crystal lamella and a greater percentage of crystal lamella relative to amorphous lamella are formed due to the exposure to low temperatures which are retained, thus reducing the drug release rate of a bioactive agent.

As used herein, "percent crystallinity" refers to the percentage of the polymer material that is in a crystalline form. Those of ordinary skill in the art understand that there are several methods for determining the percent crystallinity in polymers. These methods are, for example, described in L. H. Sperline, Introduction to Physical Polymer Science (3rd ed. 2001). The first involves the determination of the heat of fusion of the whole sample by calorimetric methods. The heat of fusion per mole of crystalline material can be estimated independently by melting point depression experiments.

A second method involves the determination of the density of the crystalline portion via X-ray analysis of the crystal structure, and determining the theoretical density of a 100% crystalline material. The density of the amorphous material can be determined from an extrapolation of the density from the melt to the temperature of interest. Then the percent crystallinity is given by:

$$\% \text{ Crystallinity} = \frac{\rho_{expt1} - \rho_{amorph}}{\rho_{100\% \, cryst} - \rho_{amorph}} \times 100$$

where $\rho_{expt1}$ represents the experimental density, and $\rho_{amorph}$ and $\rho_{100\% \, cryst}$ are the densities of the amorphous and crystalline portions, respectively.

A third method stems from the fact that X-ray diffraction depends on the number of electrons involved and is thus proportional to the density. Besides Bragg diffraction lines for the crystalline portion, there is an amorphous halo caused by the amorphous portion of the polymer. The amorphous halo occurs at a slightly smaller angle than the corresponding crystalline peak, because the atomic spacings are larger. The amorphous halo is broader than the corresponding crystalline peak, because of the molecular disorder. This third method can be quantified by the crystallinity index, CI, where $$CI = \frac{A_c}{A_a + A_c}.$$

and where $A_c$ and $A_a$ represent the area under the Bragg diffraction line and corresponding amorphous halo, respectively.

As used herein, "increased population of crystal lamella" refers to an increased number of crystal lamella from amorphous lamella by subjecting the coating to an electric polarization.

As used herein, "low temperature" refers to a temperature below 0° C., e.g., dry ice temperature (−78.5° C.), or liquid nitrogen temperature (−210° C. to −196° C.).

As used herein, "elevated temperature" refers to a temperature about 0° C. or above, e.g., a temperature higher than 0° C. but below room temperature (25° C.), or below body temperature (37° C.), or below a higher temperature, for a sufficiently short time that drug degradation and/or loss of crystallinity is within acceptable bounds, e.g., less than 90% or 95%.

In some embodiments, the piezoelectric coating can include any polymers that are piezoelectric.

As used herein, the term piezoelectric or piezoelectricity refers to the attributes of a polymer capable of generating cyclic deformation upon application of a cyclic voltage. In some embodiments, the electricity can be applied as direct current (DC) of low amplitude provided by a high voltage device to induce or modify the piezoelectric or piezoelectricity attributes of a polymer.

The term "poled" refers to the molecules of a polymer being oriented toward a direction.

In some embodiments, the piezoelectric coating can include a bioactive agent. Some examples of the bioactive agent include siRNA and/or other oligoneucleotides that inhibit endothelial cell migration. The bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction. Some other exemplary bioactive agents are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, prodrugs thereof, co-drugs thereof, and combinations thereof.

The coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

Piezoelectric Coating

The piezoelectric coating described herein can include any piezoelectric polymer or material. In some embodiments, the coating can include a piezoelectric polymer. In some embodiments, the coating can include a piezoelectric material that is not a polymer.

Piezoelectric Polymer

The piezoelectric polymer that can be included in a piezoelectric coating described herein can be any piezoelectric polymer. In some embodiments, the piezoelectric polymer is a fluoropolymer. Some examples of fluoropolymers include polyfluoroolefins such as Solef™ polymers. One example of SOLEF™ polymers is poly(vinylidene fluoride) (PVDF). PVDF is semi-crystalline polymer commercially available as powder, pellets or films. PVDF can be synthesized by addition polymerization of the $CH_2=CF_2$ monomer. The polymerization, however, is not completely regiospecific, so that the polymer contains occasional reversed monomer units (head-to-head and tail-to-tail) in the otherwise completely head-to-tail sequence. The $CF_2$ groups are referred as the "head" and the $CH_2$ groups as the "tail".

In some embodiments, the piezoelectric polymer is a copolymer of PVDF such as poly(vinylidene fluoride-co-hexafluoropropylene) (PVDF-HFP) produced by polymerizing vinylidene fluoride (VDF) with hexafluoropropylene (HFP).

Examples of piezoelectric polymers include, but are not limited to, poly(vinylidene fluoride) (PVDF), copolymers of PVDF such as poly(vinylidene fluoride-co-hexafluoropropylene) (PVDF-HFP), poly(vinylidene fluoride-co-trifluoroethylene) (PVDF-TrFE), poly(vinylidene fluoride-co-tetrafluoroethylene) (PVDF-TFE), polyamides, nylon-11, polyureas, polyurea-9, liquid crystalline polymers, biopolymers such as collagen, polypeptides, poly-methylglutamate, poly-benzyl-L-glutamate, synthetic polypeptides, oriented films of DNA, poly-lactic acid, chitin, poly(vinyl chloride) (PVC), poly(vinyl acetate) (PVAc), poly(acrylonitrile) (PAN), poly(vinylidenecyanide-co-vinyl acetate) (PVDCN-VAc), poly(vinylidenecyanide-co-vinyl benzoate) (PVDCN-VBz), poly(vinylidenecyanide-co-methyl methacrylate) (PVDCN-MMA), poly(phenylethernitrile) (PPEN), poly(1-bicyclobutanecarbonitrile), nitrile-substituted polyimides such as (—CN) APB/ODPA polyimide, aromatic polyamides, aliphatic polyurethane, polyparaxylene, poly-bis-chloromethyloxetane (Pentone), polysulfone, polyvinyl fluoride and cyanoethyl cellulose.

Piezoelectric Material

The piezoelectric material other than the piezoelectric polymer described above can be any piezoelectric material. In some embodiments, the piezoelectric material is a piezoelectric ceramic compound.

Examples of piezoelectric materials include, but are not limited to, barium titanate, lead zirconate titanate, lead niobate, berlinite, gallium orthophosphate, tourmaline, zinc oxide, aluminum nitride, lithium tantalate, lead metaniobate, lanthanum gallium silicate, potassium sodium tartrate, cadmium sulfide, bismuth titanate, lead lanthanum zirconate titanate, lead scandium tantalate, barium strontium titanate, lead magnesium niobate, quartz or combination thereof. Some further examples of piezoelectric materials include, but are not limited to, $Pb(xZr,(1-x)Ti)O_3$, $BaTiO_3$, $PbZrO_3$, $PbTiO_3$, $PbNb_2O_6$, $(Pb, Ca)TiO_3$, $(Pb,Sm)TiO_3$, $Pb(NbO_2)_2/PbTiO_3$, $(1-x)Pb(Mg_{1/3} Nb_{2/3})O_3-xPbTiO_3$, $(1-x-y)Pb(Zn_{1/3}Nb_{2/3})O_3-xPbTiO_3-yBaTiO_3$, and $(1-x-y)Pb(Zn_{1/3}Nb_{2/3})O_3-xBaTiO_3-yPbTiO_3$, xPZN-(1-x)PMN, xPMN-(1-x)PZT, PNN-PZ-PT, xPZN-(1-x)PZT, or combinations thereof.

Other piezoelectric materials that can be included in a piezoelectric coating include, but are not limited to, polymer-ceramic composites, which can be a blend or multi-layer composites. Generally, a polymer-ceramic composite includes a piezoelectric phase and a non-piezoelectric phase. The piezoelectric phase includes at least one piezoelectric material, and the non-piezoelectric phase includes a binder material which can be, e.g., a polymer. An example of such a multi-layer composite contains a PVDF and a piezoelectric ceramic. Some other examples of such polymer-ceramic composites or multi-layer composites are described in U.S. Pat. Nos. 5,505,870; and 5,796,207, the teachings of which are incorporated herein in its entirety by reference.

In some embodiments, the piezoelectric coating can specifically exclude any of the above listed piezoelectric material or materials.

Electric Polarization

The piezoelectric coating described herein can be formed onto an implantable device (e.g., a stent) and then subjected to high electric voltage. The high electric voltage can pole the piezoelectric polymer or material to orient the polymer(s) or material(s), resulting in polarization of the piezoelectric polymer(s) or material(s).

Generally, the piezoelectric coating receiving a high electric voltage treatment will be in a condition that is capable of allowing the piezoelectric polymer(s) or material to re-orient or to polarize. Such condition can include, e.g., solvated or wetted condition. In some embodiments, such condition can be, e.g., heating the coating to a temperature at or above glass transition temperature ($T_g$) of the coating.

Polarization of the piezoelectric polymer(s) or material(s) in the coating can be fixed or frozen in the coating by causing the coating to solidify from a less solidified condition by, e.g., evaporation of solvent in the coating or cooling the coating from a temperature above, e.g., $T_g$ of the coating to a temperature below $T_g$ of the coating. Following implant of an implantable device comprising the piezoelectric coating, the cyclic motion of the vessel will induce faster healing for that the coronary artery behaves like a peristaltic pump, oscillations in charge are induced due to pulsatile flow. This pulsatile flow promotes vascular healing.

As used herein, the term "high voltage" refers to a direct current (DC) having a voltage at about (e.g., 100 V) or above. The term "low voltage" refers to a DC current having a voltage at about 10V or below, e.g. 3V.

As used herein, the terms "treated", "subjected" or "delivered" relative to a voltage refers to the application of an electric field across the treated, subjected or delivered object or substrate, which is generally the coating.

Some examples of treating the piezoelectric coating by a high electric voltage are described below:

a) A piezoelectric coating comprising a piezoelectric polymer or material can be subjected to high electric voltage before the coating is dried (e.g., in a convection oven). The high electric voltage can pole and orient the piezoelectric polymer or material and cause the polarization to fix when the coating is dried. For example, a coating comprising PVDF can be subjected to the treatment of a high electric voltage in this fashion.

b) A piezoelectric coating formed on an implantable device comprising a piezoelectric polymer(s) or material(s) can be exposed to a solvent vapor (e.g., acetone vapor) and simultaneously or subsequently subjected to the treatment of a high electric voltage to re-orient to generate polarization of the piezoelectric polymer(s) or material(s). Removal of the solvent vapor and dry the coating, which may take in some solvent as the result of exposure to the solvent vapor, can cause the piezoelectric polymer(s) or material(s) to fix the polarization. The solvent for forming the solvent vapor is chosen on the condition that such solvent can solvate or wet the piezoelectric coating subjected to the treatment of high electric voltage. A person of ordinary skill in the art can readily choose a solvent to form a solvent vapor based on the chemical nature of the piezoelectric coating. For example, for a piezoelectric coating comprising PVDF, acetone or any other solvent that can solvate or wet PVDF can be used to form the solvent vapor.

c) Immediately after each coating pass, a high voltage pulse can be delivered to a piezoelectric coating thus formed comprising a piezoelectric polymer(s) or material(s). The pulses are so synchronized so that the polarization relaxation time of the piezoelectric polymer(s) or material(s) exceeds the drying time so that the polarization is fixed or frozen in the coating. Generally, the high voltage pulses can have a voltage as described above and a duration of approximately ten second or less, about one second or less, or about 0.1 second or less. The pulses can be synchronized, and a person of ordinary skill in the art can readily appreciate the ways to synchronize the pulses to cause the polarization relaxation time of the piezoelectric polymer(s) or material(s) to exceed the drying time so that the polarization is fixed or frozen in the coating.

d) During coating, a composition comprising a piezoelectric polymer(s) or material(s) onto an implantable device, a high voltage pulse can be delivered to the coating. The pulses are so synchronized so that the polarization relaxation time of the piezoelectric polymer(s) or material(s) exceeds the drying time so that the polarization is fixed or frozen in the coating. Generally, high voltage pulses can have a voltage as described above and a duration of approximately ten second or less, about one second or less, or about 0.1 second or less. The pulses can be synchronized, and a person of ordinary skill in the art can readily appreciate the ways to synchronize the pulses to cause the polarization relaxation time of the piezoelectric polymer(s) or material(s) to exceed the drying time so that the polarization is fixed or frozen in the coating.

The methods of coating an implantable device are well documented in the art. Generally, the method includes (a) providing a coating composition and (b) applying the coating composition onto an implantable medical device to form a coating on the implantable medical device. The coating composition can include any polymer(s), material(s), and bioactive agent for forming the piezoelectric coating described herein.

FIG. 1 illustrates an embodiment of the presently preferred direct contact piezoelectric polarization method using PVDF-HFP polymer:

a) place the stent over the electrically conducting metal pipe, cover and compress it with the 2 or 3-part contact or holder such that the stent's outer diameter (OD) is in direct contact with the holder and its inner diameter (ID) is in direct contact with the conducting pipe;

b) replace the vacuum chamber dome, turn on the vacuum source/pump until the air is sufficiently evacuated from the vacuum chamber and from around the stent which prevents arcing during polarization;

c) turn the directing valve of the pipes which are connected to the heated air source. Turn on the heated air source and heat the stent to a predetermined temperature. Polarization is facilitated at elevated temperatures that are below a critical temperature;

d) turn on the high voltage DC power supply to a predetermined voltage (about $50\text{-}80 \times 10^6$ volts/meter of stent coating thickness between the 2 or 3-part contact or holder and the conducting pipe). The polarization is performed;

e) after a predetermined time, turn off the heated air source and turn the directing valve so the pipes are connected to the liquid nitrogen source. Turn on the liquid nitrogen source and cool down the stent for a predetermined time. Turn off the liquid nitrogen source;

f) after a predetermined time, turn the directing valve of the pipes which are connected to the heated air source. Turn on the heated air source and heat the stent to a predetermined temperature;

g) repeat steps e) and f) number of times;

h) after a predetermined time, turn off the high voltage DC power supply;

i) turn off the vacuum source/pump and return the vacuum chamber to atmospheric pressure; and j) remove the vacuum chamber dome and remove the stent from the holder and pipe.

In some embodiments, there can be many variations to the procedure and the set-up. For instance, the stent may be dipped into liquid nitrogen and then mounted into the vacuum chamber followed by polarization. In another embodiment, the set-up remains the same, but a cooled gas like, $CO_2$ is used instead of liquid nitrogen. In some embodiments, if the stent is metallic/a conductor, then part of the stent may exposed, provided a contact and/or not coated and connected to one side of the high voltage DC power supply and the conducing pipe and 2 or 3 part holder connected to the other side of the high voltage DC power supply and the voltage adjusted appropriately for one half the total coating thickness across the stent. In some embodiments, a single cooling and warming cycle may be employed.

Biocompatible polymers

The piezoelectric coating described herein can include one or more biocompatible polymer other than the piezoelectric polymer(s) or material(s) described above. The biocompatible polymer can be biodegradable (either bioerodable or bioabsorbable) or nondegradable and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly(ether ester), polyalkylene oxalates, polyphosphazenes, phosphoryl choline, choline, poly(aspirin), polymers and copolymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one or more of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

Bioactive Agents

In embodiments, a coating described herein can optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, or antioxidant properties.

These agents can be cystostatic agents, agents that promote the healing of the endothelium (other than by releasing or generating NO), or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substance include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable. In other embodiments, the piezoelectric coating can include a chemoattractant for endothelial cells. In some embodiments, the coatings described herein can exclude any one of the above listed bioactive agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Devices

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g., FINELINE® and ENDOTAK,®, available from Guidant Corporation, Santa Clara, Calif.), and devices facilitating anastomosis such as anastomotic connectors. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

The medical device described herein is useful for a variety of medical procedures, including, by way of example, treatment of obstructions caused by tumors in the bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of controlling release rate of a bioactive agent from an implantable medical device, comprising:
   a) providing a coating on an implantable medical device, the coating comprising a bioactive agent and one or more piezoelectric polymer(s) or material(s) comprising crystal lamella;
   b) exposing the coating to a low temperature to increase crystallinity of the coating; and
   c) subjecting the coating to a high DC voltage to polarize the piezoelectric polymer(s) or material(s) so as to increase the population of the crystal lamella by converting amorphous lamella into crystal lamella, thereby reducing the release rate of the bioactive agent from the coating.

2. The method of claim 1, wherein subjecting the coating to the high DC voltage comprises subjecting the coating to the high DC voltage to polarize the piezoelectric polymer(s) or material(s) so as to increase the population of the crystal lamella by converting amorphous lamella into crystal lamella, thereby reducing the release rate of the bioactive agent from the coating at an elevated temperature.

3. The method of claim 2, wherein the elevated temperature is below body temperature.

4. The method of claim 2, wherein the elevated temperature is about 0° C.

5. The method of claim 2, wherein the elevated temperature is about room temperature.

6. The method of claim 1, wherein the low temperature is about the boiling point of liquid nitrogen.

7. The method of claim 1, wherein the low temperature is about the temperature of dry ice.

8. The method of claim 1, wherein the coating comprises at least one piezoelectric polymer.

9. The method of claim 8, wherein the at least one piezoelectric polymer is a copolymer comprising units derived from fluoro vinyl monomers.

10. The method of claim 9, wherein the at least one piezoelectric polymer comprises poly(vinylidene fluoride-co-hexafluoropropylene) (PVDF-HFP).

11. The method of claim 8, wherein the at least one piezoelectric polymer is selected from the group consisting of poly(vinylidene fluoride) (PVDF), poly(vinylidene fluoride-co-hexafluoropropylene) (PVDF-HFP), poly(vinylidene fluoride-co-trifluoroethylene) (PVDF-TrFE), poly(vinylidene fluoride-co-tetrafluoroethylene) (PVDF-TFE), polyamides, nylon-11, polyureas, polyurea-9, liquid crystalline polymers, biopolymers, collagen, polypeptides, polymethylglutamate, poly-benzyl-L-glutamate, synthetic polypeptides, oriented films of DNA, poly-lactic acid, chitin, poly(vinyl chloride) (PVC), poly(vinyl acetate) (PVAc), poly(acrylonitrile) (PAN), poly(vinylidenecyanide-co-vinyl acetate) (PVDCN-VAc), poly(vinylidenecyanide-co-vinyl benzoate) (PVDCN-VBz), poly(vinylidenecyanide-co-methyl methacrylate) (PVDCN-MMA), poly(phenyletherni-trile) (PPEN), poly(1-bicyclobutanecarbonitrile), nitrile-substituted polyimides, (—CN)APB/ODPA polyimide, aromatic polyamides, aliphatic polyurethane, polyparaxylene, poly-bis-chloromethyloxetane (Pentone), polysulfone, polyvinyl fluoride, cyanoethyl cellulose, and combinations thereof.

12. The method of claim 1, wherein the coating comprises at least one piezoelectric material.

13. The method of claim 12, wherein the at least one piezoelectric material comprises a piezoelectric ceramic or a piezoelectric polymer-ceramic composite.

14. The method of claim 1, wherein the implantable medical device is stent.

15. The method of claim 1, wherein the bioactive agent is selected from the group consisting of paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), α-hiridun, clobetasol, pimecrolimus, imatinib mesylate, midostaurin, and prodrugs thereof, co-drugs thereof, and combinations thereof.

16. The method of claim 1, wherein the coating further comprises a chemo-attractant for endothelial cells.

17. The method of claim 16, wherein the chemo-attractant is RGD or cyclic RGD peptide.

18. The method of claim 1, wherein the high DC voltage is from about 50 to about 80 million volts per meter of coating thickness.

19. The method of claim 1, wherein exposing the coating to the low temperature occurs prior to subjecting the coating to the high DC voltage.

20. The method of claim 1, wherein the high DC voltage is about 100 V or greater.

* * * * *